US009233899B2

(12) United States Patent
Weiner et al.

(10) Patent No.: US 9,233,899 B2
(45) Date of Patent: *Jan. 12, 2016

(54) HYDROGENATION CATALYSTS HAVING AN AMORPHOUS SUPPORT

(75) Inventors: Heiko Weiner, Pasadena, TX (US); Zhenhua Zhou, Houston, TX (US); Victor J. Johnston, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 715 days.

This patent is subject to a terminal disclaimer.

(21) Appl. No.: 13/552,036

(22) Filed: Jul. 18, 2012

(65) Prior Publication Data

US 2013/0165703 A1 Jun. 27, 2013

Related U.S. Application Data

(60) Provisional application No. 61/579,089, filed on Dec. 22, 2011.

(51) Int. Cl.
| | | |
|---|---|---|
| *C07C 29/149* | (2006.01) |
| *B01J 37/08* | (2006.01) |
| *B01J 37/18* | (2006.01) |
| *B01J 23/62* | (2006.01) |
| *B01J 37/02* | (2006.01) |
| *B01J 23/02* | (2006.01) |
| *B01J 35/00* | (2006.01) |
| *B01J 35/10* | (2006.01) |

(52) U.S. Cl.
CPC ............ *C07C 29/149* (2013.01); *B01J 23/626* (2013.01); *B01J 37/0201* (2013.01); *B01J 37/08* (2013.01); *B01J 37/18* (2013.01); *B01J 23/02* (2013.01); *B01J 35/002* (2013.01); *B01J 35/1019* (2013.01); *B01J 35/1042* (2013.01)

(58) Field of Classification Search
CPC ..................................................... C07C 29/149
USPC ........................................................ 568/885
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Karl et al. |
| 3,702,886 A | 11/1972 | Argauer et al. |
| 3,729,429 A | 4/1973 | Robson |
| 3,864,284 A | 2/1975 | Clippinger et al. |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz et al. |
| 4,317,918 A | 3/1982 | Takano et al. |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. |
| 4,521,630 A | 6/1985 | Wattimena et al. |
| 4,550,185 A | 10/1985 | Mabry et al. |
| 4,581,473 A | 4/1986 | Polichnowski et al. |
| 4,613,700 A | 9/1986 | Maki et al. |
| 4,620,050 A | 10/1986 | Cognion et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,843,170 A | 6/1989 | Isshiki et al. |
| 4,886,905 A | 12/1989 | Larkins et al. |
| 4,978,778 A | 12/1990 | Isshiki et al. |
| 4,985,572 A | 1/1991 | Kitson et al. |
| 4,990,655 A | 2/1991 | Kitson et al. |
| 5,061,671 A | 10/1991 | Kitson et al. |
| 5,137,861 A | 8/1992 | Shih et al. |
| 5,149,680 A | 9/1992 | Kitson et al. |
| 5,155,084 A | 10/1992 | Horn et al. |
| 5,185,308 A | 2/1993 | Bartley et al. |
| 5,233,099 A | 8/1993 | Tabata et al. |
| 5,241,106 A | 8/1993 | Inoue et al. |
| 5,243,095 A | 9/1993 | Roberts et al. |
| 5,306,845 A | 4/1994 | Yokohama et al. |
| 5,350,504 A | 9/1994 | Dessau |
| 5,426,246 A | 6/1995 | Nagahara et al. |
| 5,475,144 A | 12/1995 | Watson et al. |

(Continued)

FOREIGN PATENT DOCUMENTS

| | | |
|---|---|---|
| CN | 102271804 | 12/2011 |
| CN | 102271805 | 12/2011 |

(Continued)

OTHER PUBLICATIONS

Office Action for U.S. Appl. No. 13/552,030 dated May 15, 2014.

(Continued)

*Primary Examiner* — Elvis O Price
(74) *Attorney, Agent, or Firm* — Kilpatrick Townsend & Stockton LLP

(57) ABSTRACT

The present invention relates to a catalyst having an amorphous support and one or more active metals. The amorphous support may comprise a support material and an amorphous support modifier, which adjusts the acidity of the support material. In preparing the amorphous catalyst, post-synthesis treatment, i.e. calcination, may be used to adjust the catalyst performance while converting acetic acid to ethanol.

11 Claims, No Drawings

(56) References Cited

U.S. PATENT DOCUMENTS

| | | |
|---|---|---|
| 5,476,827 A | 12/1995 | Ferrero et al. |
| RE35,377 E | 11/1996 | Steinberg et al. |
| 5,585,523 A | 12/1996 | Weiguny et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,204,417 B1 | 3/2001 | Fischer et al. |
| 6,232,352 B1 | 5/2001 | Vidalin et al. |
| 6,232,504 B1 | 5/2001 | Barteau et al. |
| 6,294,703 B1 | 9/2001 | Hara et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,627,770 B1 | 9/2003 | Cheung et al. |
| 6,632,330 B1 | 10/2003 | Colley et al. |
| 6,670,490 B1 | 12/2003 | Campos et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B2 | 8/2006 | Huber et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,518,014 B2 | 4/2009 | Kimmich et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2006/0019360 A1 | 1/2006 | Verser et al. |
| 2006/0102520 A1 | 5/2006 | Lapinski et al. |
| 2006/0106246 A1 | 5/2006 | Warner et al. |
| 2006/0127999 A1 | 6/2006 | Verser et al. |
| 2008/0207953 A1 | 8/2008 | Houssin et al. |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0209786 A1 | 8/2009 | Scates et al. |
| 2009/0221725 A1 | 9/2009 | Chorney et al. |
| 2009/0326080 A1 | 12/2009 | Chornet et al. |
| 2010/0016454 A1 | 1/2010 | Gracey et al. |
| 2010/0029995 A1 | 2/2010 | Johnston et al. |
| 2010/0113843 A1 | 5/2010 | Lee et al. |
| 2010/0121114 A1 | 5/2010 | Johnston et al. |
| 2010/0168493 A1 | 7/2010 | Le Peltier et al. |
| 2010/0196789 A1 | 8/2010 | Fisher et al. |
| 2010/0249479 A1 | 9/2010 | Berg-Slot et al. |
| 2011/0004033 A1 | 1/2011 | Johnston et al. |
| 2011/0060169 A1 | 3/2011 | Kaizik et al. |
| 2011/0082322 A1 | 4/2011 | Jevtic et al. |
| 2011/0257443 A1 | 10/2011 | Weiner et al. |

FOREIGN PATENT DOCUMENTS

| | | |
|---|---|---|
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 6-116182 | 4/1994 |
| JP | 10-306047 | 11/1998 |
| JP | 2001-046874 | 2/2001 |
| JP | 2001-157841 | 6/2001 |
| WO | WO 83/03409 | 10/1983 |
| WO | 03/045844 A1 | 6/2003 |
| WO | WO 2009/009322 | 1/2009 |
| WO | WO 2009/009323 | 1/2009 |
| WO | WO 2009/063176 | 5/2009 |
| WO | WO 2009/105860 | 9/2009 |
| WO | WO 2010/055285 | 5/2010 |

OTHER PUBLICATIONS

Office Action for corresponding Chinese Appl. No. 201280002886.2 dated May 5, 2014.

International Preliminary Report on Patentability for PCT/US2012/068703 mailed Jul. 3, 2014.

Final Office Action for U.S. Appl. No. 13/552,030 dated Sep. 18, 2014.

Response to Final Office Action for U.S. Appl. No. 13/552,030, filed Nov. 19, 2014.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

T. Yokoyama, et al., "Carboxylic Acids and Derivatives", Fine Chemicals through Heterogenous Catalysis, pp. 370-379.

Sarsfield, "Powder x-ray diffraction detection of crystalline phases in amorphous pharamceuticals," Advances in x-ray analysis, International Centre for Diffraction Data, US v. 49, Jan. 1, 2006, pp. 322-327.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., The formation of ketones and aldehydes from carboxylic acids, structure-activity relationship for two competitive reactions, Journal of Molecular Catalysis A: Chemical 103 Jun. 14, 1995, 175-180.

(56) References Cited

OTHER PUBLICATIONS

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Brunauer Emmett and Teller, J. Am. Chem. Soc. 60, 309 (1938).

International Search Report and Written Opinion mailed May 3, 2011 in corresponding International Application No. PCT/US2011/023379.

International Preliminary Report on Patentability mailed Aug. 7, 2012 in corresponding International Application No. PCT/US2011/023379.

Chinese Office Action mailed on Jan. 16, 2015 for CN Patent Application No. 201280002886.2, with English translation, 11 pages.

Chinese Office Action mailed on Jul. 22, 2015 for CN Patent Application No. 201280002886.2, with English translation, 14 pages.

International Search Report and Written Opinion mailed Mar. 11, 2013 in corresponding International Application No. PCT/US2012/068703.

ively viable commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

HYDROGENATION CATALYSTS HAVING AN AMORPHOUS SUPPORT

CROSS REFERENCE TO RELATED APPLICATIONS

The present invention claims priority to U.S. Provisional Application No. 61/579,089, filed Dec. 22, 2011, the entire contents and disclosures of which are hereby incorporated by reference.

FIELD OF THE INVENTION

The present invention relates to a hydrogenation catalyst having an amorphous support comprising an amorphous support modifier, and one or more active metals, and to processes for calcining the amorphous support modifiers to prepare such hydrogenation catalyst. The hydrogenation catalyst is particularly suited to converting acetic acid to ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis,* 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process using a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

SUMMARY OF THE INVENTION

In a first embodiment, the invention is directed to a hydrogenating catalyst comprising an amorphous support that comprises a support material and an amorphous support modifier selected from the group consisting of (i) alkaline earth metal oxides, (ii) alkali metal oxides, (iii) alkaline earth metal silicates, (iv) alkali metal silicates, (v) Group IIB metal oxides, (vi) Group IIB metal silicates, (vii) Group IIIB metal oxides, (viii) Group IIIB metal silicates, and mixtures thereof, provided that the amorphous support modifier introduces substantially no detectable crystallinity to the amorphous support, as determined by XRD; and one or more active metals selected from the group consisting of copper, iron, cobalt, nickel, ruthenium, rhodium, platinum, palladium, osmium, iridium, titanium, zinc, chromium, rhenium, molybdenum, tungsten, vanadium, tin, lanthanum, cerium, manganese, and gold. The amorphous support modifier may have no detectable peaks as determined by XRD. In some embodiments, less than 0.5 wt. %, e.g., less than 0.3 wt. % or less than 0.25 wt. % of the amorphous support modifier is in a crystalline phase, as determined by XRD. The support material may be amorphous and may be selected from the group consisting of silica, silica gel, alumina, titania, silica/alumina, calcium metasilicate, pyrogenic silica, high purity silica, zirconia, carbon, and mixtures thereof. The amorphous support modifier may be selected from the group consisting of oxides and silicates of any of sodium, potassium, magnesium, calcium, scandium, yttrium, and zinc. The amorphous support modifier may in some embodiments be selected from the group consisting of calcium oxide, magnesium oxide, calcium silicate, calcium metasilicate, and combinations thereof. The total weight of the amorphous support modifier may be from 0.1 wt. % to 50 wt. %, based on the total weight of the catalyst. The one or more active metals comprise a first metal selected from the group consisting of copper, iron, cobalt, nickel, ruthenium, rhodium, platinum, palladium, osmium, iridium, titanium, zinc, chromium, rhenium, and molybdenum, and a second metal selected from the group consisting of copper, molybdenum, tin, chromium, iron, cobalt, vanadium, palladium, platinum, lanthanum, cerium, manganese, ruthenium, rhenium, gold, and nickel; and further wherein the second metal is different than the first metal.

In a second embodiment, the invention is directed to a process for producing ethanol comprising: contacting a feed stream comprising acetic acid and hydrogen in a reactor at an elevated temperature with a hydrogenating catalyst, comprising: an amorphous support that comprises a support material and an amorphous support modifier selected from the group consisting of (i) alkaline earth metal oxides, (ii) alkali metal oxides, (iii) alkaline earth metal silicates, (iv) alkali metal silicates, (v) Group IIB metal oxides, (vi) Group IIB metal silicates, (vii) Group IIIB metal oxides, (viii) Group IIIB metal silicates, and mixtures thereof, provided that the amorphous support modifier introduces substantially no detectable crystallinity to the amorphous support, as determined by XRD; and one or more active metals selected from the group consisting of copper, iron, cobalt, nickel, ruthenium, rhodium, platinum, palladium, osmium, iridium, titanium, zinc, chromium, rhenium, molybdenum, tungsten, vanadium, tin, lanthanum, cerium, manganese, and gold. The amorphous support modifier may have no detectable peaks as determined by XRD. In some embodiments, less than 0.5 wt. %, e.g., less than 0.3 wt. % or less than 0.25 wt. % of the amorphous support modifier is in a crystalline phase, as determined by XRD. The support material may be amorphous and may be selected from the group consisting of silica, silica gel, alumina, titania, silica/alumina, calcium metasilicate, pyrogenic silica, high purity silica, zirconia, carbon, and mixtures thereof. The amorphous support modifier may be selected from the group consisting of oxides and silicates of any of sodium, potassium, magnesium, calcium, scandium, yttrium, and zinc. The amorphous support modifier may in some embodiments be selected from the group consisting of calcium oxide, magnesium oxide, calcium silicate, calcium metasilicate, and combinations thereof. The total weight of the amorphous support modifier may be from 0.1 wt. % to 50 wt. %, based on the total weight of the catalyst. The one or more active metals may comprise a first metal selected from the group consisting of copper, iron, cobalt, nickel, ruthenium, rhodium, platinum, palladium, osmium, iridium, titanium, zinc, chromium, rhenium, and molybdenum, and a second metal selected from the group consisting of copper, molybdenum, tin, chromium, iron, cobalt, vanadium, palladium, platinum, lanthanum, cerium, manganese, ruthenium, rhenium, gold, and nickel; and further wherein the second metal is different than the first metal. In some embodiments, acetic acid conversion is greater than 30% and selectivity to ethanol is greater than 80%. The hydrogenation may performed in a vapor phase at a temperature from 125° C. to 350° C., a pressure of 10 kPa to 3000 kPa, and a hydrogen to acetic acid molar ratio of greater than 4:1. The feed stream may be produced by gasifying a carbonaceous selected from the group consisting of oil, coal, natural gas and biomass.

DETAILED DESCRIPTION OF THE INVENTION

The present invention relates to a hydrogenation catalyst having an amorphous support comprising an amorphous support modifier and one or more active metals.

The amorphous support material comprises a support material and a support modifier. The support modifier preferably lacks crystallinity, i.e. introduces substantially no detectable crystallinity to the amorphous support and has no peaks or detectable crystallinity as determined by X-Ray diffraction techniques (XRD). In some embodiments, the amorphous support modifier contains less than 1.0 wt. % of the amorphous support modifier in the crystalline phase, e.g., less than 0.5 wt. %, less than 0.3 wt. %, less than 0.25 wt. %, less than 0.1 wt. %, less than 0.05 wt. % or less than 0.01 wt. %. In terms of ranges, the amorphous support modifier contains from 0.0001 wt. % to 1.0 wt. %, e.g., from 0.0001 wt. % to 0.5 wt. %, from 0.0001 wt. % to 0.3 wt. %, from 0.0001 wt. % to 0.1 wt. %, or from 0.0001 wt. % to 0.01 wt. % of the support in the crystalline phase. More preferably, the amorphous support modifier lacks any crystallinity as determined by XRD. The amorphous support modifier may be widely dispersed on the support material to form the amorphous support. Without being bound by theory, it is believed that when adding a support modifier having 0.5 wt. % or more crystallinity, as determined by XRD, to a support material, the crystallinity of the support modifier effects the support and thus the overall catalyst. By reducing or eliminating the crystallinity of the support modifier, the amorphous character of the support material, and thus of the overall catalyst is maintained. This amorphous character improves the catalyst life.

In one optional embodiment, the amorphous support is substantially free of zeolitic material, and preferably contains less than 1 wt. %, e.g., less than 0.5 wt. % or less than 0.1 wt. % zeolitic material.

The amorphous support comprises a support material, preferably an amorphous support material, and an amorphous support modifier that may adjust the acidity of the support. For example, the acid sites, e.g. Brønsted acid sites, on the support material may be adjusted by the amorphous support modifier to favor selectivity to ethanol during the hydrogenation of acetic acid. The acidity of the support material may be adjusted by reducing the number or reducing the availability of Brønsted acid sites on the support material. The support material may also be adjusted by having the amorphous support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. For purposes of the present invention, the use of a support containing an amorphous support modifier supports preferably adjusts the acidity of the support to make the support less acidic or more basic to favor formation of ethanol over other hydrogenation products. The amorphous support modifier may also have low volatility or no volatility.

Without being bound by theory, it is believed that due to the amorphous nature of the support, the catalyst may contain several different types of oxides and silicates, including metasilicates. At room temperatures, the support modifiers by themselves may be in a crystalline state. Preferably, the support modifier is amorphous when added to the support material, and the amorphous support modifier is substantially free of crystallinity, e.g., contains less than 0.1 wt. %, or less than 0.05 wt. %. Support modifiers present in an amorphous state on the support, for example, may be selected from the group consisting of: (i) alkaline earth metal oxides, (ii) alkali metal oxides, (iii) alkaline earth metal silicates, (iv) alkali metal silicates, (v) Group IIB metal oxides, (vi) Group IIB metal silicates, (vii) Group IIIB metal oxides, (viii) Group IIIB metal silicates, and mixtures thereof. Preferably, the amorphous support modifier is selected from the group consisting of oxides and silicates of any of sodium, potassium, magnesium, calcium, scandium, yttrium, and zinc, as well as mixtures of any of the foregoing. More preferably, the amorphous support modifier may comprise calcium oxide, magnesium oxide, calcium silicate, calcium metasilicate, and combinations thereof.

In one embodiment, the total weight of the amorphous support modifier may range from 0.1 wt. % to 50 wt. %, e.g., from 0.2 wt. % to 25 wt. %, from 1 wt. % to 20 wt. %, or from 3 wt. % to 15 wt. %, based on the total weight of the catalyst.

In one embodiment, to prepare a support with an amorphous support modifier, a precursor to the amorphous support modifier may be impregnated on a support material using an incipient wetness technique and calcined. Precursors may include, but are not limited to, oxides, nitrates, oxalates, acetates or chlorides. During the impregnation and subsequent calcinations, one or more oxides or silicates may be formed on the support material to prepare the support. The use of a solvent, such as water, glacial acetic acid, a strong acid such as hydrochloric acid, nitric acid, or sulfuric acid, or an organic solvent, may be preferred to make the impregnation solution. The resulting mixture may be stirred and added to a support material using, in which the amorphous support modifier is added to a support material having the same pore volume as the volume of the solution. Capillary action then draws the amorphous support modifier into the pores in the support material. The support containing amorphous support modifier can then be formed by drying to drive off water and any volatile components within the support solution and depositing the amorphous support modifier on the support material. Drying may occur, for example, at a temperature from 50° C. to 300° C., e.g., from 100° C. to 200° C. or about 120° C., optionally for a period from 1 to 24 hours, e.g., from 3 to 15 hours or from 6 to 12 hours.

Following drying, the support solution is subjected to a post-synthesis treatment, i.e. is calcined. The calcination temperature of the precursor to the amorphous support modifier may affect the catalyst performance, including acetic acid conversion, ethanol selectivity, productivity, and/or packing density. In a preferred embodiment, the calcination temperature for the precursor to the amorphous support modifier may range from 200° C. to 1000° C., e.g., from 350° C. to 850° C. or from 375° C. to 775° C. Calcination may be for a period from 1 to 24 hours, e.g., from 3 to 15 hours or from 6 to 12 hours. In one embodiment, calcination temperatures above 375° C. may favor selectivity to ethanol over other hydrogenation compounds, such as ethyl acetate or acetaldehyde. In another embodiment, calcination temperatures from 400° C. to 750° C., in particular from 500° C. to 600° C., may favor higher productivity of ethanol than other calcination temperatures. In another embodiment, calcination temperatures that are greater than 750° C., e.g., greater than 800° C., may increase the packing density of the catalyst. Higher packing density may be needed when there is a large pressure drop across the catalyst bed. Thus, varying the calcination temperatures may change the catalyst performance to allow one to adjust or tune the catalyst based on the required hydrogenation conditions. Advantageously, this allows adjustment of the catalyst through the amorphous support modifier instead of adjusting the active metals.

The amorphous support containing an amorphous support modifier may be extruded, pelletized, tabletized, pressed, crushed or sieved to the desired size distribution. Any of the known methods to shape the support into desired size distribution can be employed.

The catalysts of the present invention may be on any suitable support material, and more preferably an amorphous support material. In one embodiment, the support material may be an inorganic oxide. In one embodiment, the support material may be selected from the group consisting of silica, silica gel, alumina, titania, silica/alumina, calcium metasilicate, pyrogenic silica, high purity silica, zirconia, carbon, and mixtures thereof. Some of these support materials may be used as precursors to the support material, e.g., silica gel, which is preferably not used alone as a support. Preferably, the support material comprises amorphous silicaceous support materials. In preferred embodiments, the support material is present in an amount from 25 wt. % to 99 wt. %, e.g., from 30 wt. % to 98 wt. % or from 35 wt. % to 95 wt. %.

The surface area of silicaceous support materials, e.g., silica, preferably is at least about 50 $m^2/g$, e.g., at least about 100 $m^2/g$ or at least about 150 $m^2/g$ In terms of ranges, the silicaceous support materials preferably have a surface area from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support material also preferably has an average pore diameter from 5 to 100 nm, e.g., from 5 to 30 nm, from 5 to 25 nm or from about 5 to 10 nm, as determined by mercury intrusion porosimetry, and an average pore volume from 0.5 to 2.0 $cm^3/g$, e.g., from 0.7 to 1.5 $cm^3/g$ or from about 0.8 to 1.3 $cm^3/g$, as determined by mercury intrusion porosimetry.

In an optional embodiment, the support material is halogen-free, more particularly chlorine-free, i.e. the content of halogen in the support material is less than 500 wppm, or more preferably from 0.0001 to 400 wppm.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, e.g., meaning the diameter for spherical particles or equivalent spherical diameter for non-spherical particles, from 0.01 to 1.0 cm, e.g., from 0.1 to 0.7 cm or from 0.2 to 0.3 cm. Since the one or more active metal(s) that are disposed on or within the support are generally very small in size, those active metals should not substantially impact the size of the overall catalyst particles. Thus, the above particle sizes generally apply to both the size of the support as well as to the final catalyst particles.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$.

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

The amorphous support that comprises amorphous silica and oxides and silicates of calcium may also comprise impurities, examples of which include aluminum oxide, titanium oxide, and iron oxide. Preferably, ethanol productivity, selectivity, and/or conversion can be improved with amorphous supports that have low levels of acidic impurities. In one embodiment, the combination of aluminum oxide, titanium oxide, and iron oxide, are present in an amount less than 0.30 wt. %, e.g., less than 0.20 wt. %, less than 0.15 wt. %, less than 0.13 wt. %, less than 0.10 wt. %, or less than 0.08 wt. %, based on the total weight of the catalyst.

One or more active metals may also be impregnated on the support. In one embodiment, the one or more active metals are selected from the group consisting of copper, iron, cobalt, nickel, ruthenium, rhodium, platinum, palladium, osmium, iridium, titanium, zinc, chromium, rhenium, molybdenum, tungsten, vanadium, tin, lanthanum, cerium, manganese, and gold. More preferably, the one or more active metals are selected from the group consisting of cobalt, iron, nickel, platinum, palladium, titanium, zinc, chromium, molybdenum, tungsten, and tin. In some embodiments, the active metals do not include ruthenium or rhenium. The total weight of all the active metals present in the catalyst preferably is from 0.1 to 25 wt. %, e.g., from 0.1 to 15 wt. %, or from 0.1 wt. % to 10 wt. %. For purposes of the present specification, unless otherwise indicated, weight percent is based on the total weight the catalyst including metal and support.

In some embodiments, the catalyst contains at least two active metals. A first active metal may be selected from the group consisting of copper, iron, cobalt, nickel, ruthenium, rhodium, platinum, palladium, osmium, iridium, titanium, zinc, chromium, rhenium, molybdenum and tungsten. When the first metal comprises platinum, it is preferred that the catalyst comprises platinum in an amount less than 5 wt. %, e.g., less than 3 wt. % or less than 1 wt. %, due to the availability of platinum. A second active metal, which is different than the first metal, is selected from the group consisting of copper, molybdenum, vanadium, tin, chromium, iron, cobalt, vanadium, tungsten, palladium, platinum, lanthanum, cerium, manganese, ruthenium, rhenium, gold, and nickel. Additional active metals, such as cobalt, copper, vanadium, tin, chromium, zinc, palladium, and/or nickel, may also be used in some embodiments.

Preferred bimetallic combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. In some embodiments, additional metals may also be used with the bimetallic combinations. For examples, some exemplary metal combinations may also include palladium/rhenium/tin, palladium/rhenium/cobalt, palladium/rhenium/nickel, platinum/tin/palladium, platinum/tin/cobalt, platinum/tin/palladium, platinum/tin/copper, platinum/tin/chromium, platinum/tin/zinc, and platinum/tin/nickel.

When the catalyst comprises two or more active metals, e.g., a first active metal and a second active metal, the first active metal may be present in the catalyst in an amount from 0.1 to 10 wt. %, e.g. from 0.1 to 5 wt. %, or from 0.1 to 3 wt. %. The second active metal may be present in an amount from 0.1 to 20 wt. %, e.g., from 0.1 to 10 wt. %, or from 0.1 to 5 wt. %. For catalysts comprising two or more active metals, the metals may be alloyed with one another or may comprise a non-alloyed metal solution or mixture.

The preferred metal ratios may vary somewhat depending on the active metals used in the catalyst. In some embodiments, the molar ratio of the first active metal to the second active metal preferably is from 10:1 to 1:10, e.g., from 4:1 to 1:4, from 2:1 to 1:2, from 1.5:1 to 1:1.5 or from 1.1:1 to 1:1.1.

After the amorphous support modifier is added to the support material as described above, the one or more active metals may also be impregnated on to the amorphous support. A precursor of the first active metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second active metal precursor also preferably is impregnated into the support from a second metal precursor. If desired, a third metal or third metal precursor may also be impregnated into the support.

Impregnation occurs by adding, optionally drop wise, either or both the first metal precursor and/or the second metal precursor and/or additional metal precursors, preferably in suspension or solution, to the dry support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the support may occur simultaneously (co-impregnation) or sequentially. In simultaneous impregnation, the first and second metal precursors (and optionally additional metal precursors) are mixed together and added to the support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the first metal precursor is first added to the support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Generally, both from the point of view of economics and environmental aspects, aqueous solutions of soluble compounds of platinum are preferred. In one embodiment, the first metal precursor is not a metal halide and is substantially free of metal halides. Without being bound to theory, such non-(metal halide) precursors are believed to increase selectivity to ethanol. A particularly preferred precursor to platinum is platinum ammonium nitrate, $Pt(NH_3)_4(NO_4)_2$. Calcining of the solution with the support and active metal may occur, for example, at a temperature from 250° C. to 800° C., e.g., from 300° C. to 700° C., from 350° C. to 600° C. or from 350° C. to 500° C., optionally for a period from 1 to 12 hours, e.g., from 2 to 10 hours, from 4 to 8 hours or about 6 hours.

In one aspect, the "promoter" metal or metal precursor is first added to the support, followed by the "main" or "primary" metal or metal precursor. Of course the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the two principal metals, e.g., Pt and Sn.

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment there is a process for producing ethanol by hydrogenating feedstock comprising compounds selected from the group consisting of acetic acid, ethyl acetate and mixtures thereof in the presence of the catalyst. One particular preferred reaction is to make ethanol from acetic acid. The hydrogenation reaction may be represented as follows:

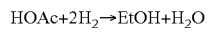

$$HOAc + 2H_2 \rightarrow EtOH + H_2O$$

The raw materials, acetic acid and hydrogen, fed to the primary reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 200 kPa to 2000 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. Generally, the reactor may use an excess of hydrogen, while the secondary hydrogenation reactor may use a sufficient amount of hydrogen as necessary to hydrogenate the impurities. In one aspect, a portion of the excess hydrogen from the reactor is directed to the secondary reactor for hydrogenation. In some optional embodiments, the secondary reactor could be operated at a higher pressure than the hydrogenation reactor and a high pressure gas stream comprising hydrogen may be separated from the secondary reactor liquid product in an adiabatic pressure reduction vessel, and the gas stream could be directed to the hydrogenation reactor system.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, the hydrogenation of acetic acid may achieve favorable conversion of acetic acid and favorable selectivity and productivity to ethanol in the primary reactor. For purposes of the present invention, the term "conversion" refers to the amount of acetic acid in the feed that is converted to a compound other than acetic acid. Conversion is expressed as a mole percentage based on acetic acid in the feed. Using calcination temperatures for the amorphous support modifier from 350° C. to 850° C., may produce a catalyst having an acetic acid conversion that is greater than 50%, e.g., greater than 80% or greater than 90%. Although catalysts that have high conversions are desirable, such as at least 50%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. In one embodiment, using calcination temperatures for the amorphous support modifier from 375° C. to 850° C. may produce a catalyst having a selectivity to ethanol is at least 70%, e.g., at least 75%, or at least 80%.

Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. In one embodiment, using calcination temperatures for the amorphous support modifier from 400° C. to 750° C. may produce a catalyst having productivity of at least 600 grams of ethanol per kilogram of catalyst per hour, e.g., at least 650 grams of ethanol per kilogram of catalyst per hour or at least 700 grams of ethanol per kilogram of catalyst per hour. In terms of ranges, the productivity preferably is from 600 to 3,000 grams of ethanol per kilogram of catalyst per hour, e.g., from 650 to 2,500 grams of ethanol per kilogram of catalyst per hour or from 700 to 2,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid calaysts, can be employed to dehydrate ethanol, as described in copending U.S. Pub. Nos. 2010/0030002 and 2010/0030001 and WO2010146332, the entire contents and disclosures of which are hereby incorporated by reference.

The following examples describe the catalyst and process of this invention.

EXAMPLES

Example 1

$Ca(OAc)_2$ Precursor

The catalyst was prepared by impregnating $Ca(OAc)_2$ on silica to make SiO2-CaO (3 wt. %). The support is then dried and calcined at 550° C.

A mixed metal precursor was prepared as follows. 1.62 g (11.38 mmol) of solid ammonium oxalate monohydrate was added to 50 ml of deionized $H_2O$ and dissolved with stirring at room temperature. 0.94 g (4.55 mmol) of tin(II) oxalate was added to the ammonium oxalate solution. The resultant mixture was stirred for another ten minutes at room temperature yielding a slightly opaque, colorless solution. 6.51 g of the platinum(II) oxalate solution (13.638 wt. % Pt) was diluted to a total volume of 18 ml using deionized $H_2O$. The dark blue platinum solution was then added to the ammonium/tin(II) solution with stirring resulting in a yellow-brown, homogeneous solution. The solution was stirred for twenty minutes at room temperature.

The mixed metal precursor was added to the modified silica support ($SiO_2$—$CaSiO_3$(3)) having a 3 mm pellet shape using the incipient wetness technique. The material was left standing for one hour at room temperature, and then evacuated to dryness in a rotor evaporator, at a slow/minimum rotation bath temperature of 80° C. The material was then dried at 120° C. overnight under circulating air.

The catalyst was then reduced using a H₂/N₂ mixture with 10 mol % of H₂ (total flow 275 sccm/min at atmospheric pressure) and the following temperature program:
(a) Room temperature to 300° C. at a 2 deg/min ramp,
(b) Hold at 300° C. for 6 hrs.
(c) Cool down to room temperature (the catalyst may alternatively be cooled to reaction temperature, if done in situ in the reactor prior to testing).

The resulting catalyst is Pt(1.0 wt. %)Sn (1.2 wt. %)/SiO₂—CaO (3 wt. %).

Example 2

Ca(NO₃)₂ Precursor

The catalyst was prepared the same as Example 1, except the precursor was calcium nitrate (Ca(NO₃)₂). The active metal loading was the same as Example 1.

Comparative A

Calcium metasilicate (about 2-5% crystallinity) was mixed with silica to form a support. Platinum and tin were impregnated on the support to form the catalyst. The active metal loading was the same as Example 1.

Example 3

Hydrogenation

Vaporized acetic acid and hydrogen were passed over each of the catalysts prepared in Ex. 1 and 2, and Comp. Ex. A. The reaction conditions were the same for each reaction. The results are indicated in Table 2.

TABLE 2

| Example | HOAc Conv. (%) | Selectivity (%) EtOH | Selectivity (%) EtOAc | EtOH Yield (%) | Productivity (g/kg/hr) |
|---|---|---|---|---|---|
| A | 71 | 81 | 15 | 57 | 619 |
| 1 | 88 | 81 | 16 | 72 | 745 |
| 2 | 88 | 85 | 13 | 75 | 739 |

Example 4

Calcination

The catalyst of Example 1 was prepared and the amorphous support modifier was calcined at different temperatures, 350° C., 450° C., 550° C., 650° C., 750° C., and 850° C. As shown in Table 3, the selectivity remained relatively unchanged from 450° C. to 850° C., however, at 350° C., the selectivity to EtOH dropped dramatically. When the EtOH selectivity is less than 100%, the balance is typically EtOAc. At 350° C., esterification is favored over hydrogenation.

TABLE 3

| Calcination Temperature | HOAc Conv. (%) | Selectivity (%) EtOH | Selectivity (%) EtOAc | Productivity (g/kg/hr) |
|---|---|---|---|---|
| 350° C. | 90 | 50 | 50 | 450 |
| 450° C. | 82 | 81 | 19 | 710 |
| 550° C. | 90 | 83 | 17 | 810 |
| 650° C. | 99 | 77 | 23 | 700 |
| 750° C. | 90 | 81 | 19 | 730 |
| 850° C. | 93 | 82 | 18 | 600 |

Example 5

Packing Density

The catalysts from Example 4 were also test for packing density. Packing density remained relatively unchanged at the temperatures of 350° C. to 650° C. However, as shown in Table 4, at the temperatures of 750° C. to 850° C., the packing density increased dramatically by about ~19%. The reactors are loaded by volume, not weight. If the packing density changes in the catalyst, then by weight, more of the 850° C. calcined catalyst is loaded into the reactor then the catalysts in the 350° C. to 650° C. calcination range. Another way to interpret overall activity of the catalyst is to represent EtOH make as a production rate (g of EtOH, per kg of catalyst, per hr). This will take the variations of catalyst weight into account.

TABLE 4

| Calcination Temperature | Packing Density (g/mL) | Productivity (g/kg/hr) |
|---|---|---|
| 350° C. | 0.37 | 450 |
| 450° C. | 0.39 | 710 |
| 550° C. | 0.37 | 810 |
| 650° C. | 0.39 | 700 |
| 750° C. | 0.4 | 730 |
| 850° C. | 0.46 | 600 |

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing ethanol comprising: contacting a feed stream comprising acetic acid and hydrogen in a reactor at an elevated temperature with a hydrogenating catalyst, comprising:
   an amorphous support that comprises a support material and an amorphous support modifier selected from the group consisting of (i) alkaline earth metal oxides, (ii) alkali metal oxides, (iii) alkaline earth metal silicates, (iv) alkali metal silicates, (v) Group IIB metal oxides, (vi) Group IIB metal silicates, (vii) Group IIIB metal oxides, (viii) Group IIIB metal silicates, and mixtures thereof, and provided that the amorphous support modifier introduces substantially no detectable crystallinity to the amorphous support as determined by XRD; and one or more active metals selected from the group consisting of copper, iron, cobalt, nickel, ruthenium, rhodium, platinum, palladium, osmium, iridium, titanium, zinc, chromium, rhenium, molybdenum, tungsten, vanadium, tin, lanthanum, cerium, manganese, and gold.

2. The process of claim 1, wherein less than 0.5 wt. % of the amorphous support modifier is in a crystalline phase, as determined by XRD.

3. The process of claim 1, wherein the amorphous support modifier is selected from the group consisting of oxides and silicates of any of sodium, potassium, magnesium, calcium, scandium, yttrium, and zinc.

4. The process of claim 1, wherein the amorphous support modifier is selected from the group consisting of calcium oxide, magnesium oxide, calcium silicate, calcium metasilicate, and combinations thereof.

5. The process of claim 1, wherein the total weight of the amorphous support modifier is from 0.1 wt. % to 50 wt. %, based on the total weight of the catalyst.

6. The process of claim 1, wherein the support material is selected from the group consisting of silica, silica gel, alumina, titania, silica/alumina, calcium metasilicate, pyrogenic silica, high purity silica, zirconia, carbon, and mixtures thereof.

7. The process of claim 1, wherein the support material is amorphous.

8. The process of claim 1, wherein the one or more active metals comprise a first metal selected from the group consisting of copper, iron, cobalt, nickel, ruthenium, rhodium, platinum, palladium, osmium, iridium, titanium, zinc, chromium, rhenium, and molybdenum, and a second metal selected from the group consisting of copper, molybdenum, tin, chromium, iron, cobalt, vanadium, palladium, platinum, lanthanum, cerium, manganese, ruthenium, rhenium, gold, and nickel; and further wherein the second metal is different than the first metal.

9. The process of claim 1, wherein acetic acid conversion is greater than 30% and wherein acetic acid selectivity to ethanol is greater than 80%.

10. The process of claim 1, wherein the hydrogenation is performed in a vapor phase at a temperature from 125° C. to 350° C., a pressure of 10 kPa to 3000 kPa, and a hydrogen to acetic acid molar ratio of greater than 4:1.

11. The process of claim 1, further comprising gasifying a carbonaceous material selected from the group consisting of oil, coal, natural gas and biomass, to produce the feed stream.

* * * * *